United States Patent [19]

Vottero et al.

[11] Patent Number: 5,113,019
[45] Date of Patent: May 12, 1992

[54] PROCESS FOR PHENOL ALKYLTHIOLATION AND ITS APPLICATION TO THE SYNTHESIS OF 4-ACYL-2-ALKYLTHIOPHENOLS

[75] Inventors: Catherine Vottero, Provins; Yves Labat, Pau; Jean-Marie Poirier, Saint-Martin Du Vivier, all of France

[73] Assignee: Societe Nationale Elf Aquitaine (Production), France

[21] Appl. No.: 607,224

[22] Filed: Nov. 5, 1990

Related U.S. Application Data

[63] Continuation of Ser. No. 281,023, Dec. 7, 1988, abandoned.

[30] Foreign Application Priority Data

Nov. 27, 1987 [FR] France .................. 87 16508
Nov. 27, 1987 [FR] France .................. 87 16509

[51] Int. Cl.$^5$ .................. C07C 319/12; C07C 45/41
[52] U.S. Cl. .................. 568/42; 568/319; 568/43
[58] Field of Search .................. 568/54, 46, 42, 43, 568/49, 319

[56] References Cited

U.S. PATENT DOCUMENTS

| | | | |
|---|---|---|---|
| 2,923,743 | 2/1960 | Delfs et al. | 568/54 |
| 4,124,722 | 11/1978 | Archer | 514/534 |
| 4,208,426 | 6/1980 | Minami et al. | 549/387 |
| 4,324,920 | 4/1982 | McKinnie et al. | 568/54 |
| 4,327,224 | 4/1982 | Archer | 560/109 |
| 4,374,149 | 2/1983 | Philion | 564/365 |

FOREIGN PATENT DOCUMENTS 627306  1/1963  France.
1544872  6/1977  United Kingdom.

OTHER PUBLICATIONS

Houben-Weyl-Methoden Der Organischen Chemie tome VII/2A, partie 1, 1973 Georg Thieme Verlag, 289-296.

"Compounds with Potential Activity Against Lethal Radiations III Boron Trifluoridecatalyzed Synthesid of Hydroxy Aryl Ketones", Buthol and Seailles, Jr. Dept. of Organic Chemistry, Radivm Institute, Univ. of Paris, pp. 606-609 (May 1955).

"Alkylmercaptophenols by Sulfenylation of Phenols", Farah and Gilbert, Allied Chemical Corp., pp. 2807-2809 (Oct. 1963).

"The Introduction of n-Alkyl Groups into Phenols and Hydroquinones", E. Armstrong et al., J. Amer. Chem. Soc., vol. 82, pp. 1928-1935 (1960).

Primary Examiner—Marianne Cintins
Assistant Examiner—Margaret Argo
Attorney, Agent, or Firm—Morgan & Finnegan

[57] ABSTRACT

The invention relates to the preparation of alkylthiophenols by reaction of a dialkyl disulphide with a phenol.

In the process according to the invention, the reaction is carried out in the presence of aluminium chloride or of ferric chloride in a solvent of the alkylbenzene type or, soley in the case of methylthiolation, in an excess of dimethyl disulphide.

This process makes it possible, in particular to obtain, with a selectivity and in a yield which are excellent, 2-alkylthiophenols which may then be converted into 4-acyl-2-alkylthiophenols by means of a reaction at a temperature ranging from 40° to 100° C. with a complex $BF_3 \cdot 2RCOOH$ where R denotes an alkyl or propenyl radical, in a proportion of 10 to 15 moles of complex per mole of 2-alkylthiophenol.

5 Claims, No Drawings

PROCESS FOR PHENOL ALKYLTHIOLATION AND ITS APPLICATION TO THE SYNTHESIS OF 4-ACYL-2-ALKYLTHIOPHENOLS

This is a continuation of co-pending application Ser. No. 07/281,023, filed Dec. 7, 1988 now abandoned.

FIELD OF THE INVENTION

The present invention relates to the preparation of alkylthiophenols by reaction of dialkyl disulphide with a phenol. More particularly, the subject of the invention is the preparation of 2-alkylthiophenols and their conversion into 4-acyl-2-alkylthiophenols.

BACKGROUND OF THE INVENTION

Alkylthiophenols are known products, used particularly as intermediates in pharmaceutical chemistry for the preparation of hypotensive and vasodilative medications, or in agrochemistry for that of herbicides or of pesticides. It is of particular importance to have access specifically to the ortho isomer or to the para isomer for these uses.

For selective preparation of each isomer, the known methods generally involve a correctly disubstituted starting material (chloronitrobenzene, nitrophenol, mercaptophenol, dichlorobenzene). These methods involve many stages and the yields obtained are often very low.

Among the many access routes to alkylthiophenols, the simplest consists in reacting a dialkyl disulphide with a phenol in the presence of a Lewis acid. However, the processes described hitherto do not make it possible to combine a good selectivity and a high degree of conversion of the starting phenol. Thus, for example, when phenol and dimethyl disulphide (DMDS) are reacted in the presence of ferric chloride or of aluminium chloride in chlorobenzene (U.S. Pat. No. 2,923,743), the ortho isomer/para isomer selectivity is only 85/15 and the yield does not exceed 48%. According to the same patent, in the absence of solvent and with a decolorizing earth (Tonsil), the para isomer predominates, but the maximum yield is 37%.

The reaction of phenol and of DMDS has also been investigated by Farah and Gilbert (Belgium Patent No. 627,306 and J. Org. Chem. 28, 2807, 1963). By using either a sulphonic acid or the $P_2O_5/H_3PO_4$ system, or, furthermore, an acidic resin (Dowex-50 sulphonated polymer) as a Lewis acid, these authors obtained degrees of conversion on the order of 20 to 30% with a para/ortho selectivity of 82/18.

More recently (Synthesis 117, 1984 and U.S. Pat. No. 4,324,920), Ranken and McKinnie have proposed to carry out the reaction of a phenol and of a dialkyl disulphide in the absence of solvent, using an aluminium phenate as catalyst. For phenol and for DMDS, this method results in an ortho/para selectivity of 71/29; and the yields of 2-methylthiophenol are about only 40%.

On the other hand, the 4-acyl-2-alkylthiophenols used as intermediates in pharmaceutical chemistry for the synthesis of hypotensive and vasodilatative medications ca be obtained in two ways. See, for example, British Patent No. 1,544,872 and U.S. Pat. Nos. 4,124,722, 4,327,224 and 4,374,149. The first, which consists in sulphochlorinating a 4-acylphenol, then reducing the sulphonyl chloride obtained to a 4-acyl-2-mercaptophenol and in treating the latter with an alkylating agent, results in low yields. Thus, when starting with 4-acetyl-phenol, the overall yield of 4-acetyl-2-methylthiophenol (or 4-hydroxy-3-methylthioacetophenone) is only 22%. The second method, which consists in acylating a 2-alkylthiophenol directly using an acyl halide under Friedel-Crafts conditions ($AlCl_3$ in nitrobenzene) affords better, but still very low yields (34% in the case of acetylation of 2-methylthiophenol to 4-hydroxy-3-methylthioacetophenone).

Acylation of phenol using a carboxylic acid in the presence of boron trifluoride was first described in 1933 by H. Meerwein (Ber. dtsch. Chem. Ges. 66, 411). Although this method has since been the subject of many investigations, among which there may be mentioned more particularly those of N. P. Buu-Hoi et al. (J. Org. Chem. 20, 606, 1955), E. C. Armstrong et al. (J. Am. Chem. Soc. 82, 1928, 1960), K. Freundenberg et al. (Ann. Chem. 590, 140, 1954) and K. Kindler et al. (Archiv der Pharmazie 287, 210, 1954), it has never yet been applied to 2-alkylthiophenols. Furthermore, under the conditions which are usually recommended by the literature (1 to 2 moles of $BF_3$/acid complex per mole of phenol), the use of this method to 2-alkylthiophenols produces only very low yields (below 40%).

The above references are hereby incorporated by reference.

It has now been found that, under certain operating conditions, the reaction of a phenol with a dialkyl disulphide enables alkylthiophenols and especially 2-alkylthiophenols to be obtained with a selectivity and in a yield which are excellent.

DETAILED DESCRIPTION OF THE INVENTION

It has also been found that 2-alkylthiophenols can be acylated by a $BF_3$/acid complex in yields which are excellent, on condition that the operation is carried out in a certain temperature range and that a high proportion of $BF_3$/acid complex is used.

The alkylthiolation process according to the invention, which consists in reacting a phenol containing at least one hydrogen atom ortho to the hydroxyl group and a linear dialkyl disulphide, is characterized in that aluminium chloride or ferric chloride is used as a Lewis acid and in that the operation is carried out in a solvent of the alkylbenzene type or, solely in the case of methylthiolation, in an excess of dimethyl disulphide.

The process according to the invention is more particularly intended for the alkylthiolation of phenol, but it can also be applied to phenols bearing one or more activating groups ($C_1$ to $C_9$ alkyl, phenyl, hydroxyl), or moderately attracting groups (for example Cl) such as para-cresol, 2,4-dimethylphenol, 4-tert-butylphenol and 2,4-di(tert-butyl)phenol, hydroquinone and para-chloro-phenol. When aluminium chloride is used as a Lewis acid, the alkylthiolation takes place essentially ortho to the hydroxyl group with an ortho/para selectivity which can reach or even sometimes exceed 95/5. With ferric chloride as a Lewis acid, the reaction takes place chiefly in a para position when the latter is free. In the contrary case, the reaction takes place in the ortho position.

The linear dialkyl disulphides in accordance with the invention may contain up to 18 carbon atoms. However, the use of dimethyl disulphide (DMDS) is preferred.

The quantity of dialkyl disulphide to be used per mole of phenol may vary from 1 to 10 moles, but is preferably between 1 and 5 moles. However, when the operation is carried out in the absence of alkylbenzene in the presence of an excess of DMDS acting as the solvent, the proportion of DMDS per mole of phenol may go up to approximately 30 moles and is advantageously between 10 and 25 moles.

The alkyl radical of the alkylbenzene solvent according to the invention may be linear or branched and may contain from 1 to 12 carbon atoms. The preferred solvent is toluene, but ethylbenzene and cumene may also be mentioned by way of examples, no limitation being implied.

The quantity of alkylbenzene solvent may vary within wide limits, but is generally between 0.2 and 4 liters per mole of phenol, preferably between 0.5 and 2 liters.

When the Lewis acid used is aluminium chloride, the latter must be used in a quantity which is at least equal to the stoichiometry and may go up to 10 moles per mole of phenol, while with ferric chloride good results are already obtained with only 0.7 mole per mole of phenol. The best results are obtained by using aluminium chloride or ferric chloride in a quantity ranging from 1 to 3 moles per mole of phenol.

The reaction, which need not be carried out under an inert atmosphere, may be conducted at a temperature ranging from approximately 0° C. up to reflux. In general, the best results are obtained by working at a temperature ranging from 25° to 120° C.

According to the present invention, 4-acyl-2-alkylthiophenols are obtained in a yield of about 80% and even higher by carrying out a reaction at a temperature ranging from 40° to 100° C. with a 2-alkylthiophenol and a complex $BF_3:2RCOOH$, in which R denotes a linear alkyl radical containing from 1 to 12 carbon atoms or a 1-propenyl radical, in a proportion of 10 to 15 moles of complex per mole of phenol.

The $BF_3:2CH_3COOH$ complex is a commercial product. The others can be prepared merely by bubbling gaseous boron trifluoride through the corresponding acid RCOOH, either at ambient temperature for liquid acids o at the melting point of the acid for compounds which are normally solid.

The acylation reaction according to the invention is performed in the absence of solvent at a temperature ranging from 40° to 100° C., preferably between approximately 60° and 80° C. The best yields are obtained when approximately 12 moles of $BF_3:2RCOOH$ complex are used per mole of 2-alkylthiophenol.

The reaction is generally very fast (about 2 to 5 hours) and its progress can be followed by gas phase chromatography. When is finished, the excess $BF_3:2RCOOH$ complex can be destroyed by treatment with water. It is more advantageous, however, to displace the excess $BF_3:2RCOOH$ complex by treatment with ether. Boron trifluoride etherate and the acid RCOOH which are formed are then trapped at a temperature of approximately 30° C. under reduced pressure (approximately 67 Pa) so as to avoid a degradation which is observed at higher temperatures. This operating procedure permits the excess boron trifluoride to be recovered.

EXAMPLES

The following examples illustrate the invention without limiting it.

EXAMPLE 1

1.6 g (12 mmol) of aluminum chloride, followed by 2.66 ml (30 mmol) or DMDS are added to a solution of 0.94 g (10 mmol) of phenol in 15 ml of toluene. The mixture, vigorously stirred, is then heated to 105° C. and kept at this temperature for 14 hours. After cooling to a temperature below 40° C., hydrolysis is carried out using 10 ml of a solution of hydrochloric acid at a concentration of 10% (by volume). The mixture is then extracted with dichloromethane (5 times 16 ml), and the solvents are then evaporated. 2-Methylthiophenol is purified by flash chromatography on 30 g of silica. The eluent used is a mixture of 100 parts by volume of petroleum ether (boiling point: 40°-60° C.) and 6 parts by volume of diethyl ether.

The purification may also be carried out on Florisil (magnesium silicate—cf. Merck Index 9th edition No. 5514). The eluent used is a mixture of petroleum ether and of diethyl ether in the volume ratio 100/1.

The yield of 2-methylthiophenol is 94%. In addition to 2-methylthiophenol, approximately 4% of 2,4-di(methylthio)phenol and 2% of phenol are recovered. There is no 4-methylthiophenol.

When the operation is carried out in the same way but with a reaction time of only 8 hours, the yield of 2-methylthiophenol is 92%.

EXAMPLE 2

1.33 g (10 mmol) of aluminium chloride, followed by 3.69 ml (30 mmol) of diethyl disulphide are added to a solution of 0.94 g of phenol in 20 ml of toluene. The suspension, vigorously stirred, is then heated to 90° C. and kept at this temperature for 6 hours.

The reaction mixture is then treated in the same way as in Example 1 and is purified on Florisil with petroleum ether as eluent. 2-Ethylthiophenol is thus obtained in an 82% yield.

EXAMPLE 3

Example 2 is repeated, but with diethyl disulphide replaced with 5.64 ml of dibutyl disulphide and holding at 100° C. for 5 hours. The purification is carried out on Florisil. The eluent used is a petroleum ether/diethyl ether mixture (volume ratio 100/3). 2-Butylthiophenol is thus obtained in a 79% yield.

EXAMPLE 4

1.6 g of aluminium chloride, followed by 2.66 ml of DMDS, are added to a solution of 1.08 g (10 mmol) or paracresol in 20 ml of toluene. The suspension, vigorously stirred, is then heated to 100° C. and kept at this temperature for 5 hours.

After the reaction mixture has been treated in the same way as in Example 1 and purified on Florisil with a petroleum ether/diethyl ether mixture (volume ratio 100/0.5) as eluent, 4-methyl-2-methylthiophenol is obtained in a 92% yield.

EXAMPLE 5

1.33 g of aluminium chloride are added to a solution of 1.1 g (10 mmol) of hydroquinone in 30 ml of DMDS. The mixture, vigorously stirred, is then heated to 105° C. and kept at this temperature for 4 hours.

The reaction mixture is then treated as in Example 1. 2-Methylthiohydroquinone is purified by flash chromatography on 30 g of silica. The eluent used is a mixture of 2 volumes of petroleum ether (bp: 40°-60° C.) and one volume of diethyl ether. The yield of 2-methylthiohydroquinone is 83%.

EXAMPLE 6

1.33 g of aluminium chloride are added to a solution of 1.29 g (10 mmol) of 4-chlorophenol in 20 ml of DMDS. Then the mixture, vigorously stirred, is heated and kept under reflux (110° C.) for 4 hours.

After treatment and purification as in Example 1, the eluent is a petroleum ether/diethyl ether mixture in the volume ratio 100/10, 4-chloro-2-methylthiophenol is obtained in an 82% yield.

EXAMPLE 7

1.33 g of aluminium chloride, followed by 1.6 ml of DMDS, are added to a solution of 1.5 g (10 mmol) of para-tert-butylphenol in 20 ml of toluene. The suspension, vigorously stirred, is then heated and kept at 100° C. for 5 hours.

After treatment and purification as in Example 1, 2-methylthiophenol is obtained in a 70% yield. The tert-butyl group has been removed.

EXAMPLE 8

Example 7 is repeated, but with aluminium chloride replaced with 1.62 g (10 mmol) of ferric chloride and with the quantity of DMDS increased to 2.66 ml. The purification is performed on Florisil with petroleum ether as eluent. 2-Methylthio-4-tert-butylphenol is thus obtained in an 83% yield.

EXAMPLE 9

1.62 g of ferric chloride are added to a solution of 2.06 g of 2,4-di(tert-butyl)phenol in 20 ml of DMDS. The suspension is then vigorously stirred for 14 hours at ambient temperature (20° C.).

After treatment as in Example 1 and purification by flash chromatography on 30 g of Florisil, the eluent used is a petroleum ether/diethyl ether mixture (volume ratio 100/1). 2,4-di(tert-butyl)-6-methylthiophenol is obtained in an 68% yield.

EXAMPLE 10

Example 4 is repeated, but with para-cresol replaced with 1.22 g of 2,4-dimethylphenol and aluminium chloride with 1.62 g of ferric chloride. The purification is performed on Florisil with a petroleum ether/diethyl ether mixture (volume ratio 100/2) as eluent. 2,4-Dimethyl-6-methylthiophenol is thus obtained in an 83% yield.

EXAMPLE 11

1.62 g of ferric chloride are added to a solution of 0.94 g of phenol in 20 ml of DMDS. The suspension, virorously stirred, is then heated to reflux (110° C.) and is kept thereat for 14 hours. It is then treated as in Example 1. 4-Methylthiophenol is purified by flash chromatography on 30 g of silica. The eluent used is a mixture of 10 parts by volume of petroleum ether (bp: 40°-60° C.) and 1 part by volume of diethyl ether.

The yield of 4-methylthiophenol is 87%. In addition, 6% of 2-methylthiophenol and 6% of phenol are recovered. There is no disubstituted derivative.

EXAMPLE 12

203.6 g of phenol and 3.25 liters of toluene are introduced into a 5-liter reactor and are then heated to reflux to dry the reactants if necessary. 346 g of anhydrous aluminium chloride and 610 g of DMDS are then added. The temperature is then maintained at 105° C. for 14 hours. After cooling, 1.1 liters of 20% strength hydrochloric acid are added. The organic phase is then separated off and the aqueous phase is extracted with dichloromethane.

After separation of the solvents and of the excess DMDS by vacuum distillation, 394 g of an organic product are obtained and are purified by distillation. Finally, 275 g of 2-methylthiophenol are collected, corresponding to a 91% yield based on the starting phenol.

EXAMPLE 13

60 mmol (11.3 g) of $BF_3:2CH_3COOH$ complex are added to 5 mmol (0.7 g) of 2-methylthiophenol. The solution is then heated to 70° C. and kept at this temperature for 3 hours. It is then hydrolyzed with 5 ml of a solution of hydrochloric acid at a concentration of 10% (by volume) and 4-hydroxy-3-methylthioacetophenone is purified by flash chromatography on 15 g of silica. The eluent used is a mixture of equal volumes of petroleum ether (bp: 40°-60° C.) and of diethyl ether.

The yield of 4-hydroxy-3-methylthioacetophenone is 87%.

EXAMPLE 14

A solution of 0.7 g of 2-methylthiophenol in 11.3 g of $BF_3:2CH_3COOH$ complex is heated to 70° C. and kept at this temperature for 3 hours. After returning to the ambient temperature, 11 ml of diethyl ether are added and vigorous stirring is applied for approximately 5 minutes before the excess ether is distilled off at atmospheric pressure. The acetic acid and boron trifluoride etherate which are formed are then trapped at approximately 30° C. at 67 Pa.

4-Hydroxy-3-methylthioacetophenone is purified as in Example 13. Yield: 86%.

EXAMPLE 15

The procedure is as in Example 13, but with the $BF_3:2CH_3COOH$ complex replaced with 12.9 g of the complex $BF_3:2C_2H_5COOH$. In this way, 4-hydroxy-3-methylthiopropiophenone is obtained in an 84% yield.

EXAMPLE 16

Example 13 is repeated, but with 2-methylthiophenol replaced with 0.77 g of 2-ethylthiophenol and using a mixture of 2 volumes of petroleum ether (bp: 40°-60° C.) and of 1 volume of diethyl ether as eluent. In this way, 3-ethylthio-4-hydroxyacetophenone is obtained in a 77% yield.

In the same way, 3-n-butylthio-4-hydroxyacetophenone is obtained in a 74% yield from 0.91 g of 2-n-butylthiophenol.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Process for the preparation of 4-acyl-2-alkylthiophenols, comprising reacting a 2-alkylthiophenol at a temperature ranging from 40° to 100° C. with a complex $BF_3:2RCOOH$ in which R denotes a linear alkyl radical containing from 1 to 12 carbon atoms or a 1-propenyl radical, in a proportion of 10 to 15 moles of complex per mole of 2-alkylthiophenol.

2. The process according to claim 1, wherein R is a methyl radical.

3. The process according to claim 1, wherein the 2-alkylthiophenol is 2-methylthiophenol.

4. The process according to claim 1, wherein approximately 12 moles of complex are used per mole of 2-alkylthiophenol.

5. The process according to claim 1, wherein the reaction is carried out at a temperature of between approximately 60° and 80° C.

* * * * *